us007863281B2

(12) United States Patent
Himmelsbach et al.

(10) Patent No.: US 7,863,281 B2
(45) Date of Patent: Jan. 4, 2011

(54) BICYCLIC HETEROCYCLES, PHARMACEUTICAL COMPOSITIONS CONTAINING THESE COMPOUNDS, THEIR USE AND PROCESSES FOR THE PREPARATION THEREOF

(75) Inventors: Frank Himmelsbach, Mittelbiberach (DE); Birgit Jung, Laupheim (DE); Flavio Solca, Vienna (AT)

(73) Assignee: Boehringer Ingelheim Pharma GmbH & Co. KG, Ingelheim Am Rhein (DE)

( * ) Notice: Subject to any disclaimer, the term of this patent is extended or adjusted under 35 U.S.C. 154(b) by 44 days.

(21) Appl. No.: 11/960,322

(22) Filed: Dec. 19, 2007

(65) Prior Publication Data
US 2008/0103161 A1 May 1, 2008

Related U.S. Application Data

(63) Continuation of application No. 11/081,067, filed on Mar. 15, 2005, now abandoned, which is a continuation of application No. 10/417,647, filed on Apr. 17, 2003, now abandoned.

(60) Provisional application No. 60/387,021, filed on Jun. 7, 2002.

(30) Foreign Application Priority Data
Apr. 19, 2002 (DE) .............................. 102 17 689

(51) Int. Cl.
*A61K 31/517* (2006.01)
*C07D 239/70* (2006.01)
(52) U.S. Cl. .................. 514/266.22; 544/253; 544/283; 514/266.1
(58) Field of Classification Search ............ 514/266.22, 514/266.1; 544/283, 253
See application file for complete search history.

(56) References Cited

U.S. PATENT DOCUMENTS

| 6,627,634 | B2 * | 9/2003 | Himmelsbach et al. | 514/266.22 |
|---|---|---|---|---|
| 6,740,651 | B2 | 5/2004 | Himmelsbach et al. | |
| 7,019,012 | B2 | 3/2006 | Himmelsbach et al. | |
| 7,220,750 | B2 | 5/2007 | Himmelsbach et al. | |
| 2001/0044435 | A1 | 11/2001 | Himmelsbach et al. | |
| 2004/0044014 | A1 | 3/2004 | Himmelsbach et al. | |
| 2005/0159436 | A1 | 7/2005 | Himmelsbach et al. | |
| 2007/0185091 | A1 | 8/2007 | Himmelsbach et al. | |
| 2008/0103161 | A1 | 5/2008 | Himmelsbach et al. | |
| 2010/0069414 | A1 | 3/2010 | Himmelsbach et al. | |

FOREIGN PATENT DOCUMENTS

| CA | 2361174 A1 | 9/2000 |
|---|---|---|
| CA | 2403152 A1 | 10/2001 |
| CA | 2417042 A1 | 3/2002 |
| CA | 2432428 A1 | 6/2002 |
| CA | 2375295 A1 | 9/2002 |
| CA | 2417907 A1 | 1/2003 |
| CA | 2484395 A1 | 10/2003 |
| DE | 19908567 A1 | 8/2000 |
| DE | 10017539 A1 | 10/2001 |
| WO | 9738983 | 10/1997 |
| WO | 9909016 | 2/1999 |
| WO | WO/00/51991 * | 2/2000 |
| WO | 0018740 A1 | 4/2000 |
| WO | 0051991 A1 | 9/2000 |
| WO | 0078735 A1 | 12/2000 |
| WO | WO 00/78735 * | 12/2000 |
| WO | 0177104 | 10/2001 |
| WO | WO 01/77104 * | 10/2001 |
| WO | 0218370 A1 | 3/2002 |
| WO | 0218376 A1 | 3/2002 |
| WO | 0250043 A1 | 6/2002 |
| WO | 03089439 A1 | 10/2003 |

OTHER PUBLICATIONS

Tsou et al, 6-substituted-4-(3-bromophenylamino) quinazolines . . . , J. Med. Chem. 2001, 44, 2719-2734.*
Pinedo et al., "Translational Research . . . ", The Oncologist 2000,, 5 (suppl1): 1-2 (www.The Oncologist .com).*
McMahon, Gerald, "VEGF Receptor Signaling in Tumor Angiogenesis", The Oncologist 2000; 5(suppl 1): 3-10 (www.The Oncologist.com).*
Tsou, et al., "6-Substituted-4-(3-bromophenylamino) quinazolines as Putative Irreversible Inhibitors of the Epidermal Growth Factor Receptor (EGFR) and Human Epidermal Growth Factor Receptor (HER-2) Tyrosine Kinases with Enhanced Antitumor Activity", J. Med. Chem, 2001, vol. 44, p. 2719-2734.
International Search Report for PCT/EP2003/03828 mailed Jul. 30, 2003.

* cited by examiner

*Primary Examiner*—Paul V. Ward
(74) *Attorney, Agent, or Firm*—Michael P. Morris; Edward S. Lazer; David A. Dow

(57) ABSTRACT

The present invention relates to bicyclic heterocycles of general formula

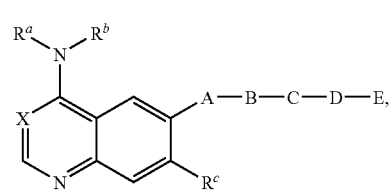

(I)

wherein
$R^a$, $R^b$, $R^c$, A, B, C, D, E and X are defined as in claim 1, the tautomers, the stereoisomers, the mixtures and the salts thereof, particularly the physiologically acceptable salts thereof with inorganic or organic acids which have valuable pharmacological properties, particularly an inhibitory effect on signal transduction mediated by tyrosine kinases, the use thereof for treating diseases, particularly tumoral diseases, as well as benign prostatic hyperplasia (BPH), diseases of the lungs and respiratory tract, and the preparation thereof.

8 Claims, No Drawings

BICYCLIC HETEROCYCLES, PHARMACEUTICAL COMPOSITIONS CONTAINING THESE COMPOUNDS, THEIR USE AND PROCESSES FOR THE PREPARATION THEREOF

RELATED APPLICATIONS

This application is a continuation of U.S. application Ser. No. 11/081,067, filed Mar. 15, 2005, which is a continuation of U.S. application Ser. No. 10/417,647, filed Apr. 17, 2003 which claims benefit of U.S. Provisional Application Ser. No. 60/387,021, filed on Jun. 7, 2002, and said Applications are herein incorporated by reference.

BACKGROUND OF THE INVENTION

The present invention relates to bicyclic heterocycles of general formula

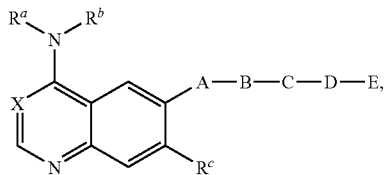

the tautomers, the stereoisomers, the mixtures and the salts thereof, particularly the physiologically acceptable salts thereof with inorganic or organic acids or bases which have valuable pharmacological properties, particularly an inhibitory effect on signal transduction mediated by tyrosine kinases, the use thereof for treating diseases, particularly tumoral diseases, as well as benign prostatic hyperplasia (BPH), diseases of the lungs and respiratory tract, and the preparation thereof.

In the above general formula I $R^a$ denotes a hydrogen atom or a $C_{1-4}$-alkyl group, $R^b$ denotes a phenyl, benzyl or 1-phenylethyl group, wherein the phenyl nucleus is substituted in each case by the groups $R^1$ to $R^3$, while $R^1$ and $R^2$, which may be identical or different, in each case denote a hydrogen, fluorine, chlorine, bromine or iodine atom, a $C_{1-4}$-alkyl, hydroxy, $C_{1-4}$-alkoxy, $C_{2-3}$-alkenyl or $C_{2-3}$-alkynyl group, an aryl, aryloxy, arylmethyl or arylmethoxy group, a heteroaryl, heteroaryloxy, heteroarylmethyl or heteroarylmethoxy group, a methyl or methoxy group substituted by 1 to 3 fluorine atoms or a cyano, nitro or amino group, and $R^3$ denotes a hydrogen, fluorine, chlorine or bromine atom, a methyl or trifluoromethyl group, $R^c$ denotes a hydrogen atom or a fluorine, chlorine or bromine atom, a hydroxy or $C_{1-4}$-alkyloxy group, a methoxy group substituted by 1 to 3 fluorine atoms, an ethyloxy group substituted by 1 to 5 fluorine atoms, a $C_{2-4}$-alkyloxy group which is substituted by a group $R^4$, where $R^4$ denotes a hydroxy, $C_{1-3}$-alkyloxy, $C_{3-6}$-cycloalkyloxy, $C_{3-6}$-cycloalkyl-$C_{1-3}$-alkyloxy, amino, $C_{1-3}$-alkylamino, di-($C_{1-3}$-alkyl)amino, bis-(2-$C_{1-3}$-alkyloxy-ethyl)-amino, bis-(3-$C_{1-3}$-alkyloxy-propyl)-amino, pyrrolidin-1-yl, piperidin-1-yl, homopiperidin-1-yl, morpholin-4-yl, homomorpholin-4-yl, piperazin-1-yl, 4-($C_{1-3}$-alkyl)-piperazin-1-yl, homopiperazin-1-yl or 4-($C_{1-3}$-alkyl)-homopiperazin-1-yl group, a $C_{2-4}$-alkyloxy group which is substituted by the group E, where E is defined as hereinafter, a $C_{3-7}$-cycloalkyloxy or $C_{3-7}$-cycloalkyl-$C_{1-4}$-alkyloxy group, a tetrahydrofuran-3-yloxy, tetrahydropyran-3-yloxy or tetrahydropyran-4-yloxy group, a tetrahydrofuranyl-$C_{1-4}$-alkyloxy or tetrahydropyranyl-$C_{1-4}$-alkyloxy group, a pyrrolidin-3-yloxy, piperidin-3-yloxy or piperidin-4-yloxy-group, a 1-($C_{1-3}$-alkyl)-pyrrolidin-3-yloxy, 1-($C_{1-3}$-alkyl)-piperidin-3-yloxy or 1-($C_{1-3}$-alkyl)-piperidin-4-yloxy-group, a $C_{1-4}$-alkoxy group which is substituted by a pyrrolidinyl, piperidinyl or homopiperidinyl group substituted in the 1 position by the group $R^5$, where $R^5$ denotes a hydrogen atom or a $C_{1-3}$-alkyl group, or a $C_{1-4}$-alkoxy group which is substituted by a morpholinyl or homomorpholinyl group substituted in the 4 position by the group $R^5$, A denotes an imino or $C_{1-4}$-alkylimino group, B denotes a carbonyl or sulphonyl group, C denotes a 1,3-allenylene, 1,1-vinylene or 1,2-vinylene group which may be substituted in each case by one or two methyl groups or by a trifluoromethyl group, an ethynylene group or a 1,3-butadien-1,4-ylene group which may be substituted by one or two methyl groups or by a trifluoromethyl group, D denotes a straight-chain or branched $C_{1-4}$-alkylene group, E denotes a pyrrolidin-1-yl group wherein two hydrogen atoms on the carbon skeleton are replaced by a straight-chain alkylene bridge, this bridge containing 2 to 6 carbon atoms if the two hydrogen atoms are located on the same carbon atom, or 1 to 5 carbon atoms if the two hydrogen atoms are located on adjacent carbon atoms, or 2 to 4 carbon atoms if the two hydrogen atoms are located on carbon atoms which are separated by one atom, while said pyrrolidin-1-yl groups may each additionally be substituted by one or two $C_{1-3}$-alkyl groups, a piperidin-1-yl or homopiperidin-1-yl group, wherein in each case two hydrogen atoms on the carbon skeleton are replaced by a straight-chain alkylene bridge, this bridge containing 2 to 6 carbon atoms if the two hydrogen atoms are located on the same carbon atom, or 1 to 5 carbon atoms if the two hydrogen atoms are located on adjacent carbon atoms, or 1 to 4 carbon atoms if the two hydrogen atoms are located on carbon atoms which are separated by one atom, or 1 to 3 carbon atoms if the two hydrogen atoms are located on carbon atoms which are separated by two atoms, while said piperidin-1-yl- and homopiperidin-1-yl groups may each additionally be substituted by one or two $C_{1-3}$-alkyl groups, a piperazin-1-yl or homopiperazin-1-yl group, wherein in each case two hydrogen atoms on the carbon skeleton are replaced by a straight-chain alkylene bridge, this bridge containing 2 to 6 carbon atoms if the two hydrogen atoms are located on the same carbon atom, or 1 to 5 carbon atoms if the two hydrogen atoms are located on adjacent carbon atoms, or 1 to 4 carbon atoms if the two hydrogen atoms are located on carbon atoms which are separated by one atom, or 1 to 3 carbon atoms if the two hydrogen atoms are located on carbon atoms which are separated by two atoms, while said piperazin-1-yl- and homopiperazin-1-yl groups may each additionally be substituted by one or two $C_{1-3}$-alkyl groups, a morpholin-4-yl or homomorpholin-4-yl group, wherein in each case two hydrogen atoms on the carbon skeleton are replaced by a straight-chain alkylene bridge, this bridge containing 2 to 6 carbon atoms if the two hydrogen atoms are located on the same carbon atom, or 1 to 5 carbon atoms if the two hydrogen atoms are located on adjacent carbon atoms, or 1 to 4 carbon atoms if the two hydrogen atoms are located on carbon atoms which are separated by one atom, or 1 to 3 carbon atoms if the two hydrogen atoms are located on carbon atoms which are separated by two atoms, while said morpholin-4-yl- and homomorpholin-4-yl may each additionally be substituted by one or two $C_{1-3}$-alkyl groups, and X denotes a methyne group substituted by a cyano group or a nitrogen atom, whilst by the aryl groups mentioned in the definition of the above groups is meant in each case a phenyl group which is mono- or disubstituted by $R^6$, while the substituents may be identical or different and $R^6$ denotes a hydrogen atom, a fluorine, chlorine, bromine or iodine atom or a $C_{1-3}$-alkyl, hydroxy, $C_{1-3}$-alkyloxy, difluoromethyl, trifluoromethyl, difluoromethoxy, trifluoromethoxy or cyano group, by the heteroaryl groups mentioned in the definition of the above groups is meant a pyridyl, pyridazinyl, pyrimidinyl or pyrazinyl group, while said heteroaryl groups are each mono- or disubstituted by the group $R^6$, while the substituents may be identical or different and $R^6$ is as hereinbefore defined, and unless otherwise stated, said alkyl groups may be straight-chained or branched.

Preferred compounds of the above general formula I are those wherein $R^a$ denotes a hydrogen atom, $R^b$ denotes a phenyl group substituted by the groups $R^1$ to $R^3$, where $R^1$ denotes a hydrogen, fluorine, chlorine or bromine atom, a methyl, trifluoromethyl or ethynyl group, a phenyloxy or phenylmethoxy group, wherein the phenyl moiety of said groups is optionally substituted by a fluorine or chlorine atom, or a pyridinyloxy or pyridinylmethoxy group, wherein the pyridinyl moiety of said groups is optionally substituted by a methyl or trifluoromethyl group, $R^2$ denotes a hydrogen, fluorine or chlorine atom and $R^3$ denotes a hydrogen atom, $R^c$ denotes a hydrogen atom, a $C_{1-3}$-alkyloxy group, a $C_{4-6}$-cycloalkyloxy or $C_{3-6}$-cycloalkyl-$C_{1-2}$-alkyloxy-group, a tetrahydrofuran-3-yloxy, tetrahydropyran-3-yloxy, tetrahydropyran-4-yloxy, tetrahydrofuranyl-$C_{1-2}$-alkyloxy or tetrahydropyranyl-$C_{1-2}$-alkyloxy group, an ethyloxy group which is substituted in the 2 position by a group $R^4$, where $R^4$ denotes a hydroxy, $C_{1-3}$-alkyloxy, amino, $C_{1-3}$-alkylamino, di-($C_{1-3}$-alkyl)amino, bis-(2-methoxyethyl)-amino, pyrrolidin-1-yl, piperidin-1-yl, homopiperidin-1-yl, morpholin-4-yl, homomorpholin-4-yl, piperazin-1-yl, 4-($C_{1-3}$-alkyl)-piperazin-1-yl, homopiperazin-1-yl, or 4-($C_{1-3}$-alkyl)-homopiperazin-1-yl group, a propyloxy group which is substituted in the 3 position by a group $R^4$, where $R^4$ is as hereinbefore defined, or a butyloxy group which is substituted in the 4 position by a group $R^4$ where $R^4$ is as hereinbefore defined, A denotes an imino group, B denotes a carbonyl or sulphonyl group, C denotes a 1,1-vinylene, 1,2-vinylene or ethynylene group, D denotes a methylene, 1,1-ethylene or 1,2-ethylene group, E denotes a piperidin-1-yl group wherein two hydrogen atoms on the carbon skeleton are replaced by a straight-chain alkylene bridge, this bridge containing 2 to 5 carbon atoms if the two hydrogen atoms are located on the same carbon atom, or 1 to 4 carbon atoms if the two hydrogen atoms are located on adjacent carbon atoms, or 1 to 3 carbon atoms if the two hydrogen atoms are located on carbon atoms which are separated by one atom, or 1 or 2 carbon atoms if the two hydrogen atoms are located on carbon atoms which are separated by two atoms, while said piperidin-1-yl groups may each additionally be substituted by one or two $C_{1-3}$-alkyl groups, a piperazin-1-yl group wherein two hydrogen atoms on the carbon skeleton are replaced by a straight-chain alkylene bridge, this bridge containing 2 to 5 carbon atoms if the two hydrogen atoms are located on the same carbon atom, or 1 to 4 carbon atoms if the two hydrogen atoms are located on adjacent carbon atoms, or 1 to 3 carbon atoms if the two hydrogen atoms are located on carbon atoms which are separated by one atom, or 1 or 2 carbon atoms if the two hydrogen atoms are located on carbon atoms which are separated by two atoms, while said piperazin-1-yl groups may each additionally be substituted by one or two $C_{1-3}$-alkyl groups, or a morpholin-4-yl group wherein two hydrogen atoms on the carbon skeleton are replaced by a straight-chain alkylene bridge, this bridge containing 2 to 5 carbon atoms if the two hydrogen atoms are located on the same carbon atom, or 1 to 4 carbon atoms if the two hydrogen atoms are located on adjacent carbon atoms, or 1 to 3 carbon atoms if the two hydrogen atoms are located on carbon atoms which are separated by one atom, or 1 or 2 carbon atoms if the two hydrogen atoms are located on carbon atoms which are separated by two atoms, while said morpholin-4-yl groups may each additionally be substituted by one or two $C_{1-3}$-alkyl groups, and X represents a nitrogen atom, while, unless otherwise stated, said alkyl groups may be straight-chain or branched, their tautomers, their stereoisomers, their mixtures and their salts.

Particularly preferred compounds of the above general formula I are those wherein $R^a$ denotes a hydrogen atom, $R^b$ denotes a 3-ethynylphenyl, 3-bromophenyl, 3,4-difluorophenyl or 3-chloro-4-fluoro-phenyl group, $R^c$ denotes a hydrogen atom, a methoxy, ethyloxy, 2-(methoxy)ethyloxy, 3-(morpholin-4-yl)propyloxy, cyclo-butyloxy, cyclopentyloxy, cyclohexyloxy, cyclopropylmethoxy, cyclopentylmethoxy, tetrahydrofuran-3-yloxy, tetrahydropyran-3-yloxy, tetrahydropyran-4-yloxy, tetrahydrofuran-2-yl methoxy, tetrahydrofuran-3-yl methoxy or tetrahydropyran-4-yl-methoxy group, A denotes an imino group, B denotes a carbonyl group, C denotes a 1,2-vinylene group, D denotes a methylene group, E denotes a 2-aza-bicyclo[2.2.1]hept-2-yl, 2,5-diaza-bicyclo[2.2.1]hept-2-yl, 5-methyl-2,5-diaza-bicyclo[2.2.1]hept-2-yl, 2-oxa-5-aza-bicyclo[2.2.1]hept-5-yl, 2-aza-bicyclo[2.2.2]oct-2-yl, 3-aza-bicyclo[3.2.1]oct-3-yl, 8-aza-bicyclo[3.2.1]oct-8-yl, 3,8-diaza-bicyclo[3.2.1]oct-3-yl, 8-methyl-3,8-diaza-bicyclo[3.2.1]oct-3-yl, 3,8-diaza-bicyclo[3.2.1]oct-8-yl, 3-methyl-3,8-diaza-bicyclo[3.2.1]oct-8-yl, 3-oxa-8-aza-bicyclo[3.2.1]oct-8-yl or 8-oxa-3-aza-bicyclo[3.2.1]oct-3-yl group and X denotes a nitrogen atom, their tautomers, their stereoisomers, their mixtures and their salts.

Most particularly preferred compounds of general formula I are those wherein $R^a$ denotes a hydrogen atom, $R^b$ denotes a 3-chloro-4-fluoro-phenyl group, $R^c$ denotes a tetrahydrofuran-3-yloxy, cyclopentyloxy or cyclopropylmethoxy group, A denotes an imino group, B denotes a carbonyl group, C denotes a 1,2-vinylene group, D denotes a methylene group, E denotes a 2-oxa-5-aza-bicyclo[2.2.1]hept-5-yl group, a 3-oxa-8-aza-bicyclo[3.2.1]oct-8-yl group or an 8-oxa-3-aza-bicyclo[3.2.1]oct-3-yl group and X denotes a nitrogen atom, their tautomers, their stereoisomers, their mixtures and their salts.

The following are mentioned as examples of particularly preferred compounds of general formula I:

(a) 4-[(3-chloro-4-fluoro-phenyl)amino]-6-{[4-((1S,4S)-2-oxa-5-aza-bicyclo[2.2.1]hept-5-yl)-1-oxo-2-buten-1-yl]amino}-7-cyclopropylmethoxy-quinazoline, (b) 4-[(3-chloro-4-fluoro-phenyl)amino]-6-{[4-((1S,4S)-2-oxa-5-aza-bicyclo[2.2.1]hept-5-yl)-1-oxo-2-buten-1-yl]amino}-7-cyclopentyloxy-quinazoline, (c) 4-[(3-chloro-4-fluoro-phenyl)amino]-6-{[4-((1S,4S)-2-oxa-5-aza-bicyclo[2.2.1]hept-5-yl)-1-oxo-2-buten-1-yl]amino}-7-[(S)-(tetrahydrofuran-3-yl)oxy]-quinazoline, (d) 4-[(3-chloro-4-fluoro-phenyl)amino]-6-{[4-(3-oxa-8-aza-bicyclo[3.2.1]oct-8-yl)-1-oxo-2-buten-1-yl]amino}-7-[(S)-(tetrahydrofuran-3-yl)oxy]-quinazoline, (e) 4-[(3-chloro-4-fluoro-phenyl)amino]-6-{[4-((1R,4R)-2-oxa-5-aza-bicyclo[2.2.1]hept-5-yl)-1-oxo-2-buten-1-yl]amino}-7-[(S)-(tetrahydrofuran-3-yl)oxy]-quinazoline, (f) 4-[(3-chloro-4-fluoro-phenyl)amino]-6-{[4-(8-oxa-3-aza-bicyclo[3.2.1]oct-3-yl)-1-oxo-2-buten-1-yl]amino}-7-[(S)-(tetrahydrofuran-3-yl)oxy]-quinazoline, (g) 4-[(3-chloro-4-fluoro-phenyl)amino]-6-{[4-((1R,4R)-2-oxa-5-aza-bicyclo[2.2.1]hept-5-yl)-1-oxo-2-buten-1-yl]amino}-7-[(R)-(tetrahydrofuran-3-yl)oxy]-quinazoline and (h) 4-[(3-chloro-4-fluoro-phenyl)amino]-6-{[4-((1S,4S)-2-oxa-5-aza-bicyclo[2.2.1]hept-5-yl)-1-oxo-2-buten-1-yl]amino}-7-[(R)-(tetrahydrofuran-3-yl)oxy]-quinazoline, and the salts thereof.

The compounds of general formula I may be prepared for example by the following methods:

a) reacting a compound of general formula

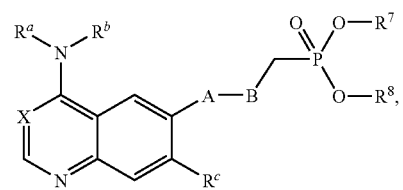
(II)

wherein $R^a$, $R^b$, $R^c$, A, B and X are as hereinbefore defined and $R^7$ and $R^8$, which may be identical or different, denote $C_{1-4}$-alkyl groups, with a compound of general formula

OHC-D-E, (III)

wherein

D and E are as hereinbefore defined.

The reaction is expediently carried out in a solvent or mixture of solvents such as tetrahydrofuran, tetrahydrofuran/water, acetonitrile, acetonitrile/water, dioxane, ethyleneglycol dimethyl ether, isopropanol, methylene chloride, dimethylformamide or sulpholane optionally in the presence of an inorganic or organic base, e.g. sodium carbonate, potassium hydroxide or 1,8-diazabicyclo[5.4.0]undec-7-ene and optionally in the presence of a lithium salt such as lithium chloride at temperatures between −50 and 150° C., but preferably at temperatures between −20 and 80° C. The reaction may also be carried out with a reactive derivative of the compound of general formula III, for example the hydrate or a hemiacetal.

b) reacting a compound of general formula

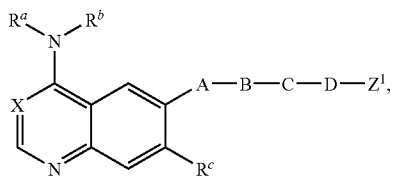

(IV)

wherein $R^a$, $R^b$, $R^c$, A, B, C, D and X are as hereinbefore defined and $Z^1$ denotes a leaving group such as a halogen atom or a substituted sulphonyloxy group such as a chlorine or bromine atom, a methanesulphonyloxy or p-toluene-sulphonyloxy group, with a compound of general formula

H-E, (V)

wherein E is as hereinbefore defined.

The reaction is expediently carried out in a solvent such as isopropanol, butanol, tetrahydrofuran, dioxane, acetonitrile, dimethylformamide, sulpholane, toluene or methylene chloride or mixtures thereof, optionally in the presence of an inorganic or organic base, e.g. sodium carbonate, potassium carbonate, potassium hydroxide, triethylamine or N-ethyl-diisopropylamine and optionally in the presence of a reaction accelerator such as an alkali metal iodide at temperatures between −20 and 150° C., but preferably at temperatures between 0 and 100° C. The reaction may, however, also be carried out without a solvent or in an excess of the compound of general formula V used.

In the reactions described hereinbefore, any reactive groups present such as hydroxy, amino, alkylamino or imino groups may be protected during the reaction by conventional protecting groups which are cleaved again after the reaction.

For example, a protecting group for a hydroxy group may be a trimethylsilyl, acetyl, trityl, benzyl or tetrahydropyranyl group.

Protecting groups for an amino, alkylamino or imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group, for example.

Any protecting group used is optionally subsequently cleaved for example by hydrolysis in an aqueous solvent, e.g. in water, isopropanol/water, acetic acid/water, tetrahydrofuran/water or dioxan/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane optionally using a solvent such as methylene chloride, dioxan, methanol or diethyl ether.

A trifluoroacetyl group is preferably cleaved by treating with an acid such as hydrochloric acid, optionally in the presence of a solvent such as acetic acid at temperatures between 50 and 120° C. or by treating with sodium hydroxide solution, optionally in the presence of a solvent such as tetrahydrofuran at temperatures between 0 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyl-tartaric acid, malic acid, mandelic acid, camphorsulphonic acid, glutamic acid, aspartic acid or quinic acid. An optically active alcohol may be for example (+) or (−)-menthol and an optically active acyl group in amides may be a (+)- or (−)-menthyloxycarbonyl, for example.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

As already mentioned hereinbefore, the compounds of general formula I according to the invention and the physiologically acceptable salts thereof have valuable pharmacological properties, particularly an inhibiting effect on signal transduction mediated by the Epidermal Growth Factor receptor (EGF-R), whilst this may be achieved for example by inhibiting ligand bonding, receptor dimerisation or tyrosine kinase itself. It is also possible that the transmission of signals to components located downstream is blocked.

The biological properties of the new compounds were investigated as follows:

The inhibition of human EGF-receptor kinase was determined using the cytoplasmic tyrosine kinase domain (methionine 664 to alanine 1186 based on the sequence published in Nature 309 (1984), 418). For this the protein was expressed in Sf9 insect cells as GST fusion protein using the Baculovirus expression system.

The enzyme activity was measured in the presence or absence of the test compounds in serial dilutions. The polymer pEY (4:1) obtained from SIGMA was used as the substrate. Biotinylated pEY (bio-pEY) was added as the tracer substrate. 100 μl of reaction solution contained 10 μl of the inhibitor in 50% DMSO, 20 μl of the substrate solution (200 mM HEPES pH 7.4, 50 mM magnesium acetate, 2.5 mg/ml poly(EY), 5 μg/ml bio-pEY) and 20 μl of enzyme preparation. The enzyme reaction was started by the addition of 50 μl of a 100 μM ATP solution in 10 mM of magnesium chloride. The dilution of the enzyme preparation was adjusted so that the incorporation of phosphate in the bio-pEY was linear in terms of time and quantity of enzyme. The enzyme preparation was diluted in 20 mM HEPES pH 7.4, 1 mM EDTA, 130 mM common salt, 0.05% Triton X-100, 1 mM DTT and 10% glycerol.

The enzyme assays were carried out at ambient temperature over a period of 30 minutes and ended by the addition of 50 μl of a stopping solution (250 mM EDTA in 20 mM HEPES pH 7.4). 100 μl were placed on a streptavidin-coated microtitre plate and incubated for 60 minutes at ambient temperature. Then the plate was washed with 200 μl of a wash solution (50 mM Tris, 0.05% Tween 20). After the addition of 100 μl of an HRPO-labelled anti-PY antibody (PY20H Anti-PTyr:HRP made by Transduction Laboratories, 250 ng/ml) the preparation was incubated for 60 minutes. Then the microtitre plate was washed three times with 200 μl of wash solution. The samples were then combined with 100 μl of a TMB-peroxidase solution (A:B=1:1, Kirkegaard Perry Laboratories). After 10 minutes the reaction was stopped. The extinction was measured at $OD_{450nm}$ with an ELISA reader. All the results were measured three times.

The data were adapted by iterative calculation using an analytical programme for sigmoid curves (Graph Pad Prism Version 3.0) with a variable Hill pitch. All the iterative data produced had a correlation coefficient of more than 0.9 and the upper and lower values of the curves showed a spread of at least a factor of 5. The active substance concentration which inhibits the activity of EGF receptor kinase by 50% ($IC_{50}$) was derived from the curves.

The following results are shown in Table I:

TABLE I

| Compound (Example No.) | Inhibition of EGF-receptor kinase $IC_{50}$ [nM] |
|---|---|
| 1 | 1.5 |
| 1(1) | 0.5 |
| 2 | 0.5 |
| 2(2) | 0.5 |
| 2(3) | 2 |

The compounds of general formula I according to the invention thus inhibit signal transduction by tyrosine kinases, as demonstrated by the example of the human EGF receptor, and are therefore useful for treating pathophysiological processes caused by hyperfunction of tyrosine kinases. These are e.g. benign or malignant tumours, particularly tumours of epithelial and neuroepithelial origin, metastasisation and the abnormal proliferation of vascular endothelial cells (neoangiogenesis).

The compounds according to the invention are also useful for preventing and treating diseases of the airways and lungs which are accompanied by increased or altered production of mucus caused by stimulation by tyrosine kinases, e.g. in inflammatory diseases of the airways such as chronic bronchitis, chronic obstructive bronchitis, asthma, bronchiectasis, allergic or non-allergic rhinitis or sinusitis, cystic fibrosis, α1-antitrypsin deficiency, or coughs, pulmonary emphysema, pulmonary fibrosis and hyperreactive airways.

The compounds are also suitable for treating diseases of the gastrointestinal tract and bile duct and gall bladder which are associated with disrupted activity of the tyrosine kinases, such as may be found e.g. in chronic inflammatory changes such as cholecystitis, Crohn's disease, ulcerative colitis, and ulcers in the gastrointestinal tract or such as may occur in diseases of the gastrointestinal tract which are associated with increased secretions, such as Ménétrier's disease, secreting adenomas and protein loss syndrome.

In addition, the compounds of general formula I and the physiologically acceptable salts thereof may be used to treat other diseases caused by abnormal function of tyrosine kinases, such as e.g. epidermal hyperproliferation (psoriasis), benign prostatic hyperplasia (BPH), inflammatory processes, diseases of the immune system, hyperproliferation of haematopoietic cells, etc.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g. etoposide), mitosis inhibitors (e.g. vinblastine), compounds which interact with nucleic acids (e.g. cis-platin, cyclophosphamide, adriamycin), hormone antagonists (e.g. tamoxifen), inhibitors of metabolic processes (e.g. 5-FU etc.), cytokines (e.g. interferons), antibodies, etc. For treating respiratory tract diseases, these compounds may be used on their own or in conjunction with other therapeutic agents for the airways, such as substances with a secretolytic (e.g. ambroxol, N-acetylcysteine), broncholytic (e.g. tiotropium or ipratropium or fenoterol, salmeterol, salbutamol) and/or anti-inflammatory activity (e.g. theophylline or glucocorticoids). For treating diseases in the region of the gastrointestinal tract, these compounds may also be administered on their own or in conjunction with substances having an effect on motility or secretion. These combinations may be administered either simultaneously or sequentially.

These compounds may be administered either on their own or in conjunction with other active substances by intravenous, subcutaneous, intramuscular, intraperitoneal or intranasal route, by inhalation or transdermally or orally, whilst aerosol formulations are particularly suitable for inhalation.

For pharmaceutical use the compounds according to the invention are generally used for warm-blooded vertebrates, particularly humans, in doses of 0.01-100 mg/kg of body weight, preferably 0.1-15 mg/kg. For administration they are formulated with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof in conventional galenic preparations such as plain or coated tablets, capsules, powders, suspensions, solutions, sprays or suppositories.

The following Examples are intended to illustrate the present invention without restricting it:

Preparation of the Starting Compounds:

EXAMPLE I

4-[(3-chloro-4-fluoro-phenyl)amino]-6-[(diethoxy-phosphoryl)-acetylamino]-7-[(S)-(tetrahydrofuran-3-yl)oxy]-quinazoline 60.07 g of diethoxyphosphorylacetic acid are placed in 750 ml N,N-dimethylformamide and at ambient temperature combined with 48.67 g of N,N'-carbonyldiimidazole. After the development of gas has ended 90.00 g of 4-[(3-chloro-4-fluoro-phenyl)amino]-6-amino-[(S)-(tetrahydrofuran-3-yl)oxy]-quinazoline are added and the reaction mixture is stirred for about 4-5 hours at ambient temperature until the reaction is complete. The reaction mixture is then heated gently in a water bath and two batches of 750 ml of water are added. The thick suspension is stirred overnight and the next morning another 350 ml of water are added. The suspension is cooled in the ice bath, stirred for another hour and suction filtered. The filter cake is washed with 240 ml of N,N-dimethylformamide/water (1:2) and 240 ml of diisopropylether and dried at 40° C. in a circulating air drier.

Yield: 117.30 g (88% of theory)

$R_f$ value: 0.37 (silica gel, methylene chloride/methanol=9:1)

Mass spectrum (ESI$^+$): m/z=553, 555 [M+H]$^+$

The following compound is obtained analogously to Example I:

(1) 4-[(3-chloro-4-fluoro-phenyl)amino]-6-[(diethoxy-phosphoryl)-acetylamino]-7-[(R)-(tetrahydrofuran-3-yl)oxy]-quinazoline Mass spectrum (ESI$^+$): m/z=553, 555 [M+H]$^+$

EXAMPLE II (1S,4S)-(2-oxa-5-aza-bicyclo[2.2.1]hept-5-yl)-acetaldehyde-hydrochloride Prepared by treating (1S,4S)-5-(2,2-dimethoxy-ethyl)-2-oxa-5-aza-bicyclo[2.2.1]heptane with conc. hydrochloric acid in water at 80° C. The solution obtained is further reacted directly in Example 2 and 2(5).

The following compounds are obtained analogously to Example II:

(1) (3-oxa-8-aza-bicyclo[3.2.1]oct-8-yl)-acetaldehyde-hydrochloride

The solution obtained is further reacted directly in Example 2(1).

(2) (1R,4R)-(2-oxa-5-aza-bicyclo[2.2.1]hept-5-yl)-acetaldehyde-hydrochloride

The solution obtained is further reacted directly in Example 2(2) and 2(4).

(3) (8-oxa-3-aza-bicyclo[3.2.1]oct-3-yl)-acetaldehyde-hydrochloride

The solution obtained is further reacted directly in Example 2(3).

EXAMPLE III (1S,4S)-5-(2,2-dimethoxy-ethyl)-2-oxa-5-aza-bicyclo[2.2.1]heptane Prepared by reacting (1S,4S)-2-oxa-5-aza-bicyclo[2.2.1]heptane-hydrochloride with bromoacetaldehyde-dimethylacetal in the presence of potassium carbonate in N-methylpyrrolidinone at 100° C.

$R_f$ value: 0.35 (silica gel, methylene chloride/methanol/conc. aqueous ammonia=90:10:1)

Mass spectrum (ESI$^+$): m/z=188 [M+H]$^+$

The following compounds are obtained analogously to Example III:

(1) 8-(2,2-dimethoxy-ethyl)-3-oxa-8-aza-bicyclo[3.2.1]octane $R_f$ value: 0.81 (silica gel, methylene chloride/methanol/conc. aqueous ammonia=90:10:1)

(2) (1R,4R)-5-(2,2-dimethoxy-ethyl)-2-oxa-5-aza-bicyclo[2.2.1]heptane $R_f$ value: 0.23 (silica gel, ethyl acetate/methanol/conc. aqueous ammonia=90:10:1)

Mass spectrum (ESI$^+$): m/z=188 [M+H]$^+$

The (1R,4R)-2-oxa-5-aza-bicyclo[2.2.1]heptane-hydrochloride used is prepared by reacting (2R,4R)-1-(tert.-butyloxycarbonyl)-2-[(4-methylphenyl-sulphonyloxy)-methyl]-4-hydroxy-pyrrolidine (see J. Org. Chem., 1992, 57, 3783-3789) with sodium hydride in tetrahydrofuran and subsequently treating it with hydrochloric acid in dioxane.

(3) 3-(2,2-dimethoxy-ethyl)-8-oxa-3-aza-bicyclo[3.2.1]octane $R_f$ value: 0.84 (silica gel, ethyl acetate/methanol/conc. aqueous ammonia=90:10:1)

Preparation of the Final Compounds:

EXAMPLE 1

4-[(3-chloro-4-fluoro-phenyl)amino]-6-{[4-((1S,4S)-2-oxa-5-aza-bicyclo[2.2.1]hept-5-yl)-1-oxo-2-buten-1-yl]amino}-7-cyclopropylmethoxy-quinazoline

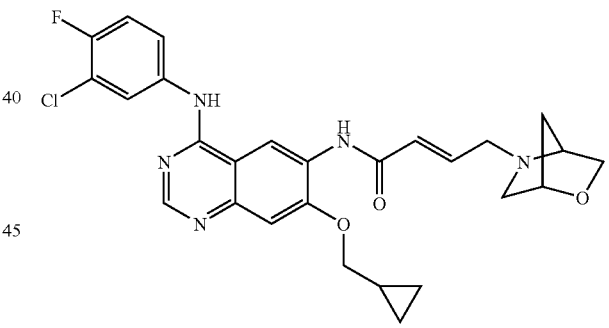

4.50 g of bromocrotonic acid are dissolved in 40 ml of methylene chloride and combined with 4.70 ml of oxalyl chloride. After the addition of 0.02 ml of N,N-dimethylformamide a vigorous development of gas sets in which is finished after about two hours. The reaction mixture is evaporated down in vacuo and the flask residue is dissolved in 40 ml methylene chloride. This solution is added dropwise to a mixture of 7.00 g of 4-[(3-chloro-4-fluoro-phenyl)amino]-6-amino-7-cyclopropylmethoxy-quinazoline and 9.60 ml of Hünig base in 80 ml of tetrahydrofuran while cooling with an ice bath. The reaction solution is stirred for one hour in the ice bath and for another hour at ambient temperature. One fifth of this solution is then removed and combined with 740 mg of (1S,4S)-2-oxa-5-aza-bicyclo[2.2.1]heptane-hydrochloride and 1 ml of Hünig base. The reaction mixture is stirred overnight at 60° C. and then evaporated down in vacuo. The flask residue is taken up with ethyl acetate and a little methanol and extracted with water. The organic phase is taken up on silica gel and chromatographed through a silica gel column with ethyl acetate/methanol (95:5 to 70:30) as eluant. The product obtained is crystallised from diisopropylether and suction filtered.

Yield: 850 mg (42% of theory)

$R_f$ value: 0.36 (silica gel, ethyl acetate/methanol=9:1)

Mass spectrum (ESI$^+$): m/z=524, 526 [M+H]$^+$

The following compound is obtained analogously to Example 1:

(1) 4-[(3-chloro-4-fluoro-phenyl)amino]-6-{[4-((1S,4S)-2-oxa-5-aza-bicyclo[2.2.1]hept-5-yl)-1-oxo-2-buten-1-yl]amino-7-cyclopentyloxy-quinazoline

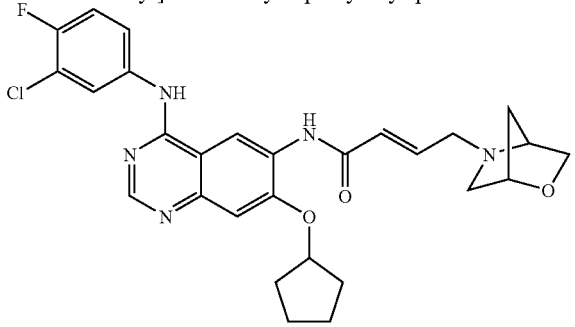

$R_f$ value: 0.40 (Reversed phase ready-made TLC plate (E. Merck), acetonitrile/water/trifluoroacetic acid=50:50:1)

Mass spectrum (ESI$^-$): m/z=536, 538 [M–H]$^-$

EXAMPLE 2

4-[(3-chloro-4-fluoro-phenyl)amino]-6-{[4-((1S,4S)-2-oxa-5-aza-bicyclo[2.2.1]hept-5-yl)-1-oxo-2-buten-1-yl]amino}-7-[(S)-(tetrahydrofuran-3-yl)oxy]-quinazoline

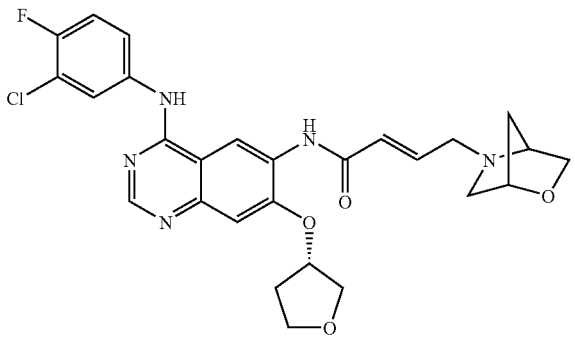

A solution of 4.44 g of 4-[(3-chloro-4-fluoro-phenyl)amino]-6-[2-(diethoxy-phosphoryl)-acetylamino]-7-[(S)-(tetrahydrofuran-3-yl)oxy]-quinazoline in 22 ml of tetrahydrofuran is added at ambient temperature to a solution of 340 mg of lithium chloride in 22 ml of water. Then 2.73 g of potassium hydroxide flakes are added and the reaction mixture is cooled to −3° C. in a cooling bath of ice and acetone. The solution of (1S,4S)-(2-oxa-5-aza-bicyclo[2.2.1]hept-5-yl)-acetaldehyde-hydro-chloride obtained in Example II is then added dropwise within 5 min at a temperature of 0° C. After the addition has ended the reaction mixture is stirred for another 10 min at 0° C. and another 20 min at ambient temperature. For working up 100 ml of ethyl acetate are added and the aqueous phase is separated off. The organic phase is washed with saturated sodium chloride solution, dried over magnesium sulphate and evaporated down. The crude product is purified by chromatography over a silica gel column with methylene chloride/methanol/conc. methanolic ammonia (980:18:2 to 750:225:25) as eluant. The product obtained is brought to crystallisation with a little diisopropylether.

Yield: 2.60 g (60% of theory)

$R_f$ value: 0.33 (silica gel, methylene chloride/methanol/conc. aqueous ammonia=90:10:1)

Mass spectrum (ESI$^+$): m/z=540, 542 [M+H]$^+$

The following compounds are obtained analogously to Example 2:

(1) 4-[(3-chloro-4-fluoro-phenyl)amino]-6-{[4-(3-oxa-8-aza-bicyclo[3.2.1]oct-8-yl)-1-oxo-2-buten-1-yl]amino}-7-[(S)-(tetrahydrofuran-3-yl)oxy]-quinazoline

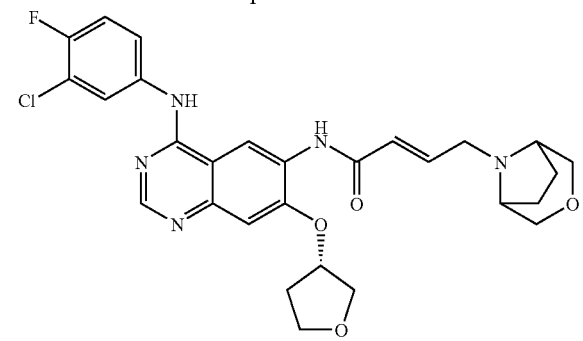

Mass spectrum (ESI$^+$): m/z=554, 556 [M+H]$^+$ (2) 4-[(3-chloro-4-fluoro-phenyl)amino]-6-{[4-((1R,4R)-2-oxa-5-aza-bicyclo[2.2.1]hept-5-yl)-1-oxo-2-buten-1-yl]amino}-7-[(S)-(tetrahydrofuran-3-yl)oxy]-quinazoline

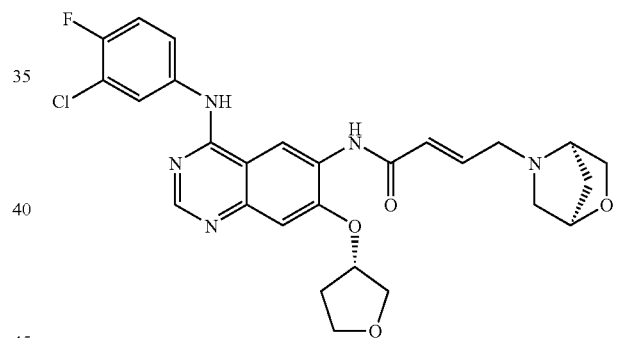

$R_f$ value: 0.08 (silica gel, ethyl acetate/methanol/conc. aqueous ammonia=90:10:1)

Mass spectrum (ESI$^-$): m/z=538, 540 [M–H]$^-$ (3) 4-[(3-chloro-4-fluoro-phenyl)amino]-6-{[4-(8-oxa-3-aza-bicyclo[3.2.1]oct-3-yl)-1-oxo-2-buten-1-yl]amino}-7-[(S)-(tetrahydrofuran-3-yl)oxy]-quinazoline

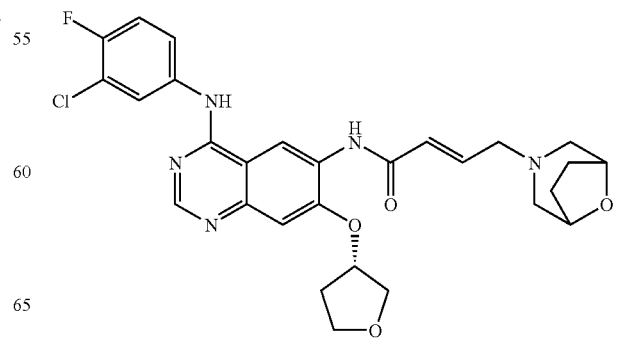

$R_f$ value: 0.77 (aluminium oxide, ethyl acetate/methanol=95:5)

Mass spectrum (ESI⁺): m/z=554, 556 [M+H]⁺

(4) 4-[(3-chloro-4-fluoro-phenyl)amino]-6-{[4-((1R,4R)-2-oxa-5-aza-bicyclo[2.2.1]hept-5-yl)-1-oxo-2-buten-1-yl]amino}-7-[(R)-(tetrahydrofuran-3-yl)oxy]-quinazoline

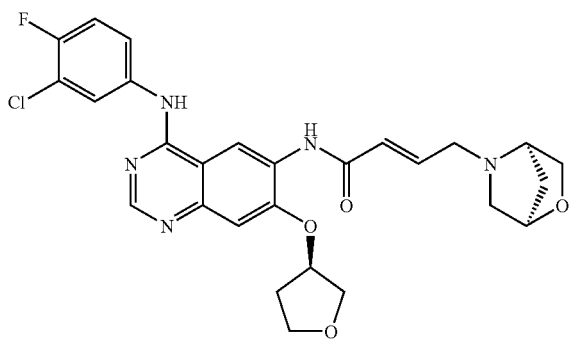

Mass spectrum (ESI⁺): m/z=540, 542 [M+H]⁺

(5) 4-[(3-chloro-4-fluoro-phenyl)amino]-6-{[4-((1S,4S)-2-oxa-5-aza-bicyclo[2.2.1]hept-5-yl)-1-oxo-2-buten-1-yl]amino}-7-[(R)-(tetrahydrofuran-3-yl)oxy]-quinazoline

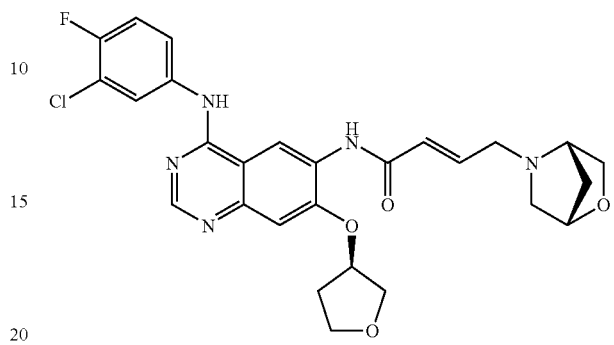

Mass spectrum (ESI⁺): m/z=540, 542 [M+H]⁺

The following compounds as shown in Table II may also be prepared analogously to the foregoing Examples and other methods known from the literature:

TABLE II

| Example No. | Structure |
|---|---|
| (1) | 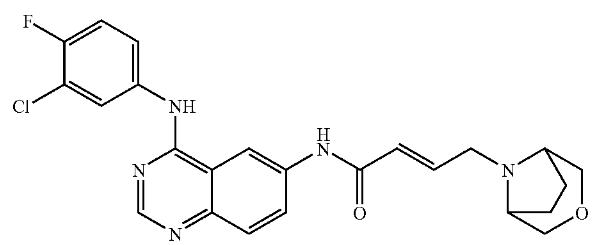 |
| (2) | 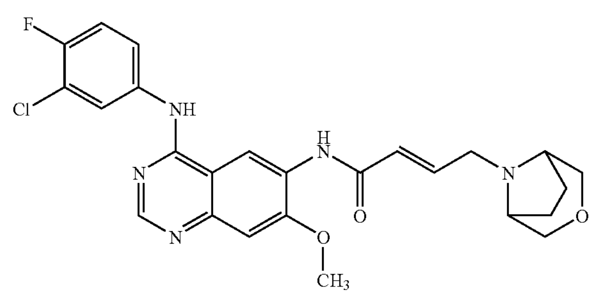 |
| (3) | 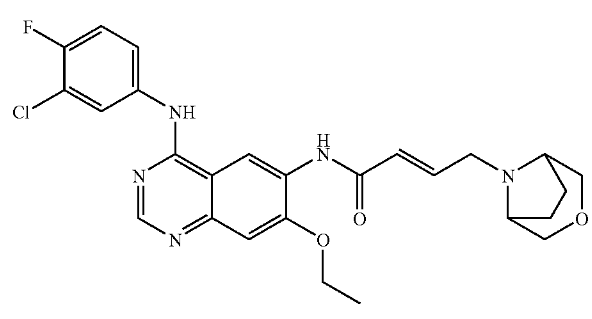 |

TABLE II-continued

| Example No. | Structure |
|---|---|
| (4) | [Structure: 4-(3-chloro-4-fluorophenylamino)-7-(2-methoxyethoxy)quinazoline with 6-NH-C(O)-CH=CH-CH2-N(2-oxa-5-azabicyclo[2.2.1]heptane) substituent] |
| (5) | [Structure: 4-(3-chloro-4-fluorophenylamino)-7-(3-morpholinopropoxy)quinazoline with 6-NH-C(O)-CH=CH-CH2-N(2-oxa-5-azabicyclo[2.2.1]heptane) substituent] |
| (6) | [Structure: 4-(3-chloro-4-fluorophenylamino)-7-cyclobutoxyquinazoline with 6-NH-C(O)-CH=CH-CH2-N(2-oxa-5-azabicyclo[2.2.1]heptane) substituent] |
| (7) | [Structure: 4-(3-chloro-4-fluorophenylamino)-7-cyclopentyloxyquinazoline with 6-NH-C(O)-CH=CH-CH2-N(2-oxa-5-azabicyclo[2.2.1]heptane) substituent] |

TABLE II-continued

| Example No. | Structure |
|---|---|
| (8) | *[structure: 4-(3-chloro-4-fluoroanilino)-7-cyclohexyloxy-quinazoline with 6-NH-C(=O)-CH=CH-CH2-(7-oxa-2-azabicyclo[2.2.1]heptane) substituent]* |
| (9) | *[structure: 4-(3-chloro-4-fluoroanilino)-7-cyclopropylmethoxy-quinazoline with 6-NH-C(=O)-CH=CH-CH2-(7-oxa-2-azabicyclo[2.2.1]heptane) substituent]* |
| (10) | *[structure: 4-(3-chloro-4-fluoroanilino)-7-cyclopentylmethoxy-quinazoline with 6-NH-C(=O)-CH=CH-CH2-(7-oxa-2-azabicyclo[2.2.1]heptane) substituent]* |
| (11) | *[structure: 4-(3-chloro-4-fluoroanilino)-7-((S)-tetrahydrofuran-3-yloxy)-quinazoline with 6-NH-C(=O)-CH=CH-CH2-(7-oxa-2-azabicyclo[2.2.1]heptane) substituent]* |

TABLE II-continued

| Example No. | Structure |
|---|---|
| (12) | 4-[(3-chloro-4-fluorophenyl)amino]-7-[(tetrahydro-2H-pyran-3-yl)oxy]-6-quinazolinyl (2E)-4-(2-oxa-5-azabicyclo[2.2.1]hept-5-yl)-2-butenamide |
| (13) | 4-[(3-chloro-4-fluorophenyl)amino]-7-[(tetrahydro-2H-pyran-4-yl)oxy]-6-quinazolinyl (2E)-4-(2-oxa-5-azabicyclo[2.2.1]hept-5-yl)-2-butenamide |
| (14) | 4-[(3-chloro-4-fluorophenyl)amino]-7-[[(2S)-tetrahydrofuran-2-yl]methoxy]-6-quinazolinyl (2E)-4-(2-oxa-5-azabicyclo[2.2.1]hept-5-yl)-2-butenamide |
| (15) | 4-[(3-chloro-4-fluorophenyl)amino]-7-[[(2R)-tetrahydrofuran-2-yl]methoxy]-6-quinazolinyl (2E)-4-(2-oxa-5-azabicyclo[2.2.1]hept-5-yl)-2-butenamide |

TABLE II-continued

| Example No. | Structure |
| --- | --- |
| (16) | [Structure: 4-(3-chloro-4-fluoroanilino)-7-(tetrahydrofuran-3-ylmethoxy)quinazoline with 6-position N-H-C(=O)-CH=CH-CH2-(2-oxa-5-azabicyclo[2.2.1]heptane) substituent] |
| (17) | [Structure: 4-(3-chloro-4-fluoroanilino)-7-(tetrahydropyran-4-ylmethoxy)quinazoline with 6-position N-H-C(=O)-CH=CH-CH2-(2-oxa-5-azabicyclo[2.2.1]heptane) substituent] |
| (18) | [Structure: 4-(3-chloro-4-fluoroanilino)quinazoline with 6-position N-H-C(=O)-CH=CH-CH2-(2-oxa-5-azabicyclo[2.2.1]heptane) substituent] |
| (19) | [Structure: 4-(3-chloro-4-fluoroanilino)-7-methoxyquinazoline with 6-position N-H-C(=O)-CH=CH-CH2-(2-oxa-5-azabicyclo[2.2.1]heptane) substituent] |

TABLE II-continued

| Example No. | Structure |
|---|---|
| (20) | 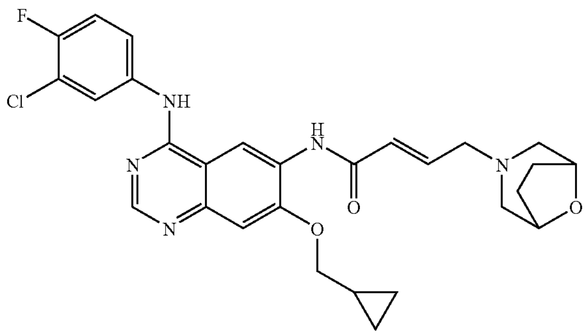 |
| (21) | 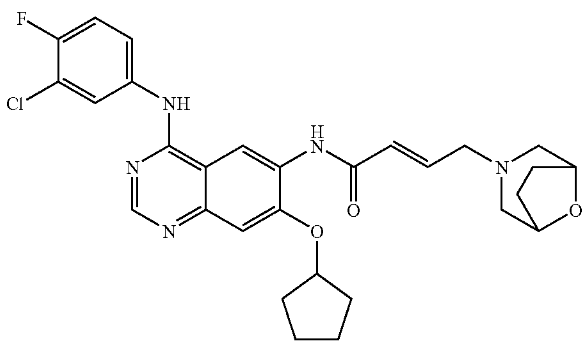 |
| (22) | 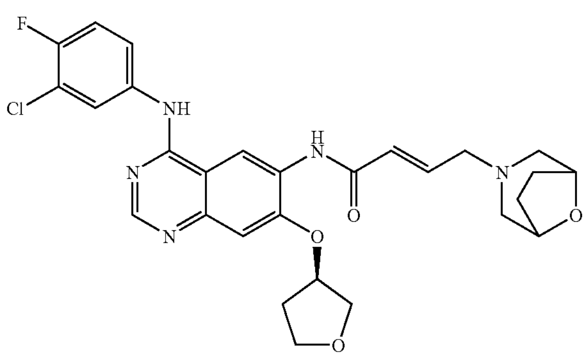 |
| (23) | 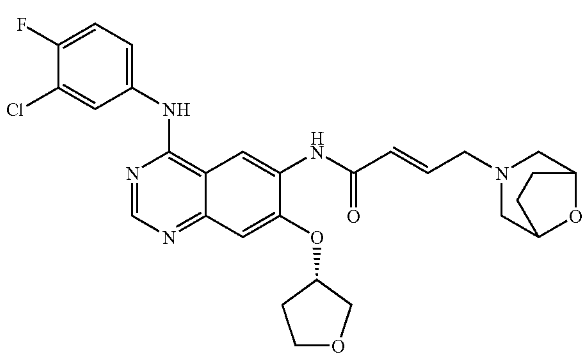 |

TABLE II-continued

| Example No. | Structure |
|---|---|
| (24) | 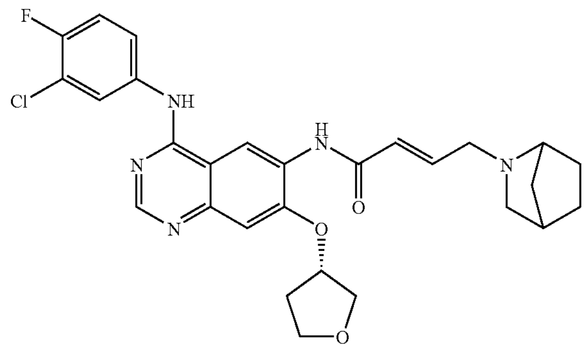 |
| (25) | 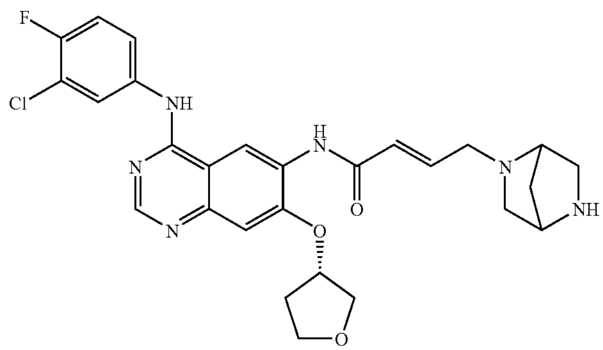 |
| (26) | 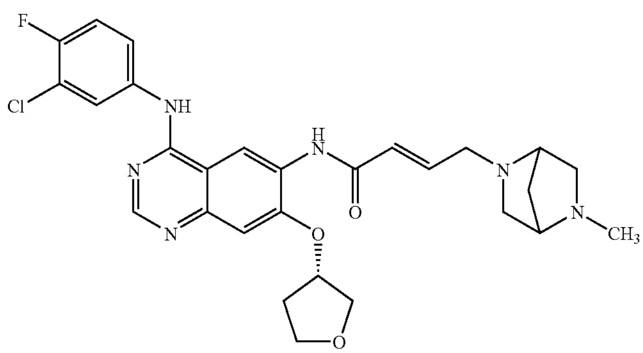 |
| (27) | 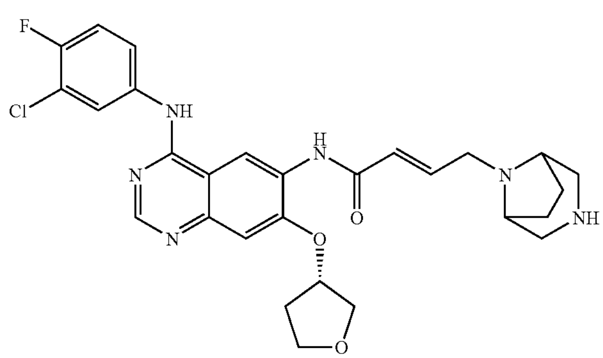 |

TABLE II-continued
| Example No. | Structure |
|---|---|
| (28) | 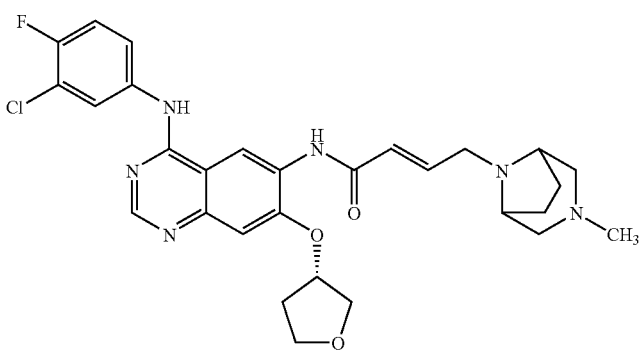 |
| (29) | 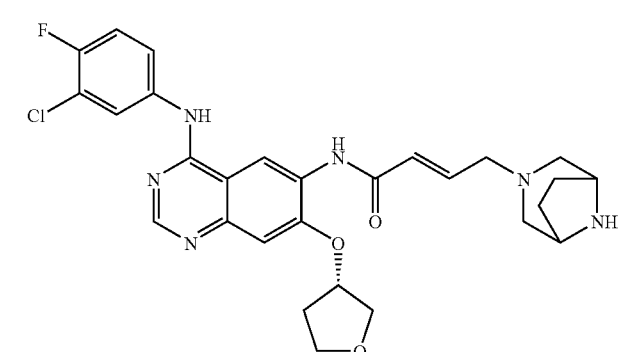 |
| (30) | 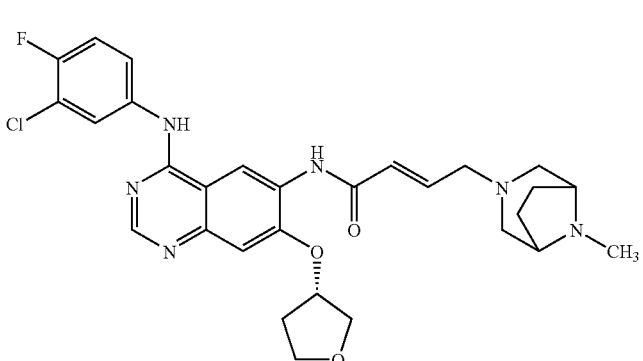 |
| (31) | 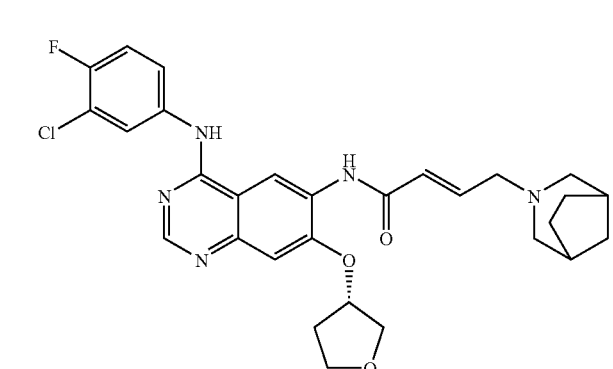 |

TABLE II-continued

| Example No. | Structure |
|---|---|
| (32) | 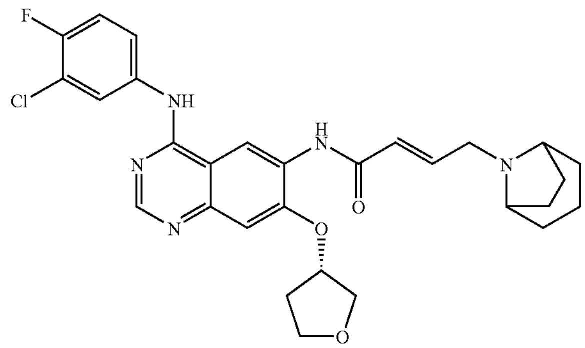 |
| (33) | 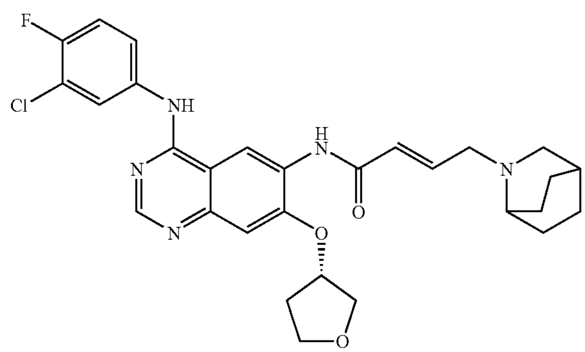 |
| (34) | 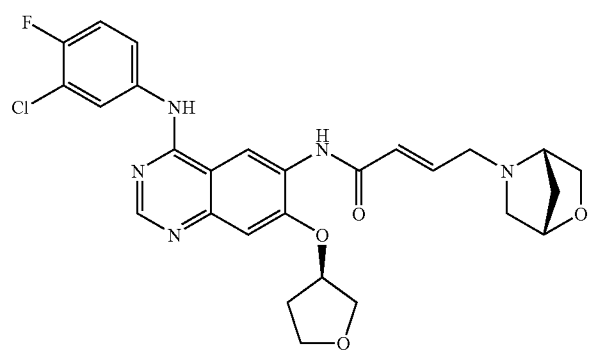 |
| (35) | 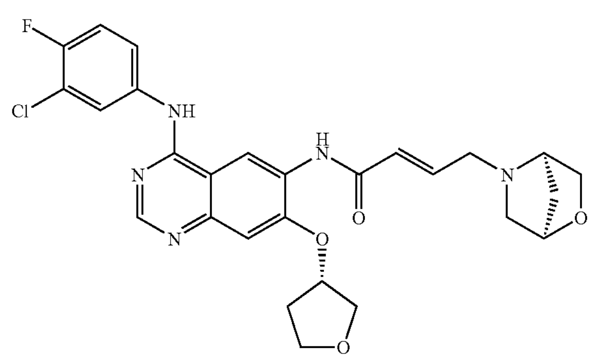 |

TABLE II-continued

| Example No. | Structure |
|---|---|
| (36) | 4-[(3-chloro-4-fluorophenyl)amino]-7-[(S)-(tetrahydrofuran-3-yl)oxy]-6-{[4-(2-oxa-5-azabicyclo[2.2.1]hept-5-yl)-2-butenoyl]amino}quinazoline |
| (37) | 4-[(3-ethynylphenyl)amino]-7-[(S)-(tetrahydrofuran-3-yl)oxy]-6-{[4-(2-oxa-5-azabicyclo[2.2.1]hept-5-yl)-2-butenoyl]amino}quinazoline |
| (38) | 4-[(3,4-difluorophenyl)amino]-7-[(S)-(tetrahydrofuran-3-yl)oxy]-6-{[4-(2-oxa-5-azabicyclo[2.2.1]hept-5-yl)-2-butenoyl]amino}quinazoline |

TABLE II-continued

| Example No. | Structure |
|---|---|
| (39) | 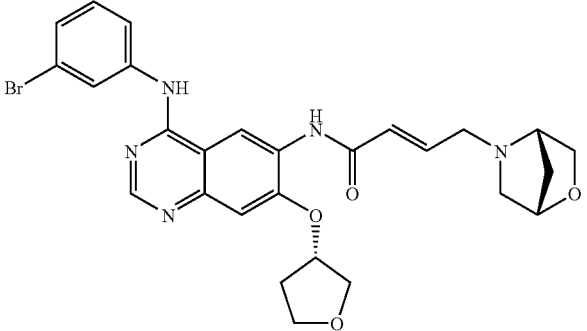 |

EXAMPLE 3

Coated Tablets Containing 75 mg of Active Substance

| 1 tablet core contains: | |
|---|---:|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 4

Tablets Containing 100 mg of Active Substance

| Composition: 1 tablet contains: | |
|---|---:|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE 5

Tablets Containing 150 mg of Active Substance

| Composition: 1 tablet contains: | |
|---|---:|
| active substance | 50.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg
die: 10 mm, flat

EXAMPLE 6

Hard Gelatine Capsules Containing 150 mg of Active Substance

| 1 capsule contains: | |
| --- | --- |
| active substance | 50.0 mg |
| corn starch (dried) | approx. 80.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

EXAMPLE 7

Suppositories Containing 150 mg of Active Substance

| 1 suppository contains: | |
| --- | --- |
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2000.0 mg |

Preparation:

After the suppository mass has been melted the active substance is homogeneously distributed therein and the melt is poured into chilled moulds.

EXAMPLE 8

Suspension Containing 50 mg of Active Substance

| 100 ml of suspension contain: | |
| --- | --- |
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 9

Ampoules Containing 10 mg Active Substance

| Composition: | |
| --- | --- |
| active substance | 10.0 mg |
| 0.01 N hydrochloric acid q.s. | |
| double-distilled water | 2.0 ml |

Preparation:

The active substance is dissolved in the necessary amount of 0.01 N HCl, made isotonic with common salt, filtered sterile and transferred into 2 ml ampoules.

EXAMPLE 10

Ampoules Containing 50 mg of Active Substance

| Composition: | |
| --- | --- |
| active substance | 50.0 mg |
| 0.01 N hydrochloric acid q.s. | |
| double-distilled water | 10.0 ml |

Preparation:

The active substance is dissolved in the necessary amount of 0.01 N HCl, made isotonic with common salt, filtered sterile and transferred into 10 ml ampoules.

EXAMPLE 11

Capsules for Powder Inhalation Containing 5 mg of Active Substance

| 1 capsule contains: | |
|---|---|
| active substance | 5.0 mg |
| lactose for inhalation | 15.0 mg |
| | 20.0 mg |

Preparation:

The active substance is mixed with lactose for inhalation. The mixture is packed into capsules in a capsule-making machine (weight of the empty capsule approx. 50 mg).

weight of capsule: 70.0 mg size of capsule=3

| 1 spray contains: | |
|---|---|
| active substance | 2.500 mg |
| benzalkonium chloride | 0.001 mg |
| 1 N hydrochloric acid q.s. | |
| ethanol/water (50/50) | 15.000 mg |

Preparation:

The active substance and benzalkonium chloride are dissolved in ethanol/water (50/50). The pH of the solution is adjusted with 1 N hydrochloric acid. The resulting solution is filtered and transferred into suitable containers for use in hand-held nebulisers (cartridges).

Contents of the container: 4.5 g

We claim:

1. A bicyclic heterocycle of formula

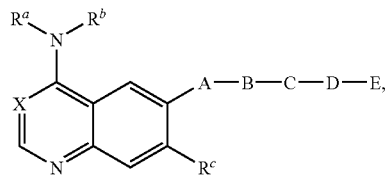

(I)

wherein $R^a$ denotes a hydrogen atom or a $C_{1-4}$-alkyl group, $R^b$ denotes a phenyl, benzyl or 1-phenylethyl group, wherein the phenyl nucleus is substituted in each case by the groups $R^1$ to $R^3$, while $R^1$ and $R^2$, which may be identical or different, in each case denote a hydrogen, fluorine, chlorine, bromine or iodine atom, a $C_{1-4}$-alkyl, hydroxy, $C_{1-4}$-alkoxy, $C_{2-3}$-alkenyl or $C_{2-3}$-alkynyl group, an aryl, aryloxy, arylmethyl or arylmethoxy group, a heteroaryl, heteroaryloxy, heteroarylmethyl or heteroarylmethoxy group, a methyl or methoxy group substituted by 1 to 3 fluorine atoms or a cyano, nitro or amino group, and $R^3$ denotes a hydrogen, fluorine, chlorine or bromine atom, a methyl or trifluoromethyl group, $R^c$ denotes a hydrogen atom or a fluorine, chlorine or bromine atom, a hydroxy or $C_{1-4}$-alkyloxy group, a methoxy group substituted by 1 to 3 fluorine atoms, an ethyloxy group substituted by 1 to 5 fluorine atoms, a $C_{2-4}$-alkyloxy group which is substituted by a group $R^4$, where $R^4$ denotes a hydroxy, $C_{1-3}$-alkyloxy, $C_{3-6}$-cycloalkyloxy, $C_{3-6}$-cycloalkyl-$C_{1-3}$-alkyloxy, amino, $C_{1-3}$-alkylamino, di-($C_{1-3}$-alkyl)amino, bis-(2-$C_{1-3}$-alkyloxy-ethyl)-amino, bis-(3-$C_{1-3}$-alkyloxy-propyl)-amino, pyrrolidin-1-yl, piperidin-1-yl, homopiperidin-1-yl, morpholin-4-yl, homomorpholin-4-yl, piperazin-1-yl, 4-($C_{1-3}$-alkyl)-piperazin-1-yl, homopiperazin-1-yl or 4-($C_{1-3}$-alkyl)-homopiperazin-1-yl group, a $C_{2-4}$-alkyloxy group which is substituted by the group E, where E is defined as hereinafter, a $C_{3-7}$-cycloalkyloxy or $C_{3-7}$-cycloalkyl-$C_{1-4}$-alkyloxy group, a tetrahydrofuran-3-yloxy, tetrahydropyran-3-yloxy or tetrahydropyran-4-yloxy group, a tetrahydrofuranyl-$C_{1-4}$-alkyloxy or tetrahydropyranyl-$C_{1-4}$-alkyloxy group, a pyrrolidin-3-yloxy, piperidin-3-yloxy or piperidin-4-yloxy-group, a 1-($C_{1-3}$-alkyl)-pyrrolidin-3-yloxy, 1-($C_{1-3}$-alkyl)-piperidin-3-yloxy or 1-($C_{1-3}$-alkyl)-piperidin-4-yloxy-group, a $C_{1-4}$-alkoxy group which is substituted by a pyrrolidinyl, piperidinyl or homopiperidinyl group substituted in the 1 position by the group $R^5$, where $R^5$ denotes a hydrogen atom or a $C_{1-3}$-alkyl group, or a $C_{1-4}$-alkoxy group which is substituted by a morpholinyl or homomorpholinyl group substituted in the 4 position by said group $R^5$, A denotes an imino or $C_{1-4}$-alkylimino group, B denotes a carbonyl or sulphonyl group, C denotes a 1,3-allenylene, 1,1-vinylene or 1,2-vinylene group which may be substituted in each case by one or two methyl groups or by a trifluoromethyl group, an ethynylene group or a 1,3-butadien-1,4-ylene group which may be substituted by one or two methyl groups or by a trifluoromethyl group, D denotes a straight-chain or branched $C_{1-4}$-alkylene group, E denotes a pyrrolidin-1-yl group wherein two hydrogen atoms on the carbon skeleton are replaced by a straight-chain alkylene bridge, this bridge containing 2 to 6 carbon atoms if the two hydrogen atoms are located on the same carbon atom, or 1 to 5 carbon atoms if the two hydrogen atoms are located on adjacent carbon atoms, or 2 to 4 carbon atoms if the two hydrogen atoms are located on carbon atoms which are separated by one atom, while said pyrrolidin-1-yl groups may each additionally be substituted by one or two $C_{1-3}$-alkyl groups, a piperidin-1-yl or homopiperidin-1-yl group, wherein in each case two hydrogen atoms on the carbon skeleton are replaced by a straight-chain alkylene bridge, this bridge containing 2 to 6 carbon atoms if the two hydrogen atoms are located on the same carbon atom, or 1 to 5 carbon atoms if the two hydrogen atoms are located on adjacent carbon atoms, or 1 to 4 carbon atoms if the two hydrogen atoms are located on carbon atoms which are separated by one atom, or 1 to 3 carbon atoms if the two hydrogen atoms are located on carbon atoms which are separated by two atoms, while said piperidin-1-yl- and homopiperidin-1-yl groups may each additionally be substituted by one or two $C_{1-3}$-alkyl groups, a piperazin-1-yl or homopiperazin-1-yl group, wherein in each case two hydrogen atoms on the carbon skeleton are replaced by a straight-chain alkylene bridge, this bridge containing 2 to 6 carbon atoms if the two hydrogen atoms are located on the same carbon atom, or 1 to 5 carbon atoms if the two hydrogen atoms are located on adjacent carbon atoms, or 1 to 4 carbon atoms if the two hydrogen atoms are located on carbon atoms which are separated by one atom, or 1 to 3 carbon atoms if the two hydrogen atoms are located on carbon atoms which are separated by two atoms, while said piperazin-1-yl- and homopiperazin-1-yl groups may each additionally be substituted by one or two $C_{1-3}$-alkyl groups, a morpholin-4-yl or homomorpholin-4-yl group, wherein in each case two hydrogen atoms on the carbon skeleton are replaced by a straight-chain alkylene bridge, this bridge containing 2 to 6 carbon atoms if the two hydrogen atoms are located on the same carbon atom, or 1 to 5 carbon atoms if the two hydrogen atoms are located on adjacent carbon atoms, or 1 to 4 carbon atoms if the two hydrogen atoms are located on carbon atoms which are separated by one atom, or 1 to 3 carbon atoms if the two hydrogen atoms are located on carbon atoms which are separated by two atoms, while said morpholin-4-yl- and homomorpholin-4-yl may each additionally be substituted by one or two $C_{1-3}$-alkyl groups, and X denotes a methyne group substituted by a cyano group or a nitrogen atom, wherein said aryl groups are in each case a phenyl group which is mono- or disubstituted by $R^6$, while the substituents may be identical or different and $R^6$ denotes a hydrogen atom, a fluorine, chlorine, bromine or iodine atom or a $C_{1-3}$-alkyl, hydroxy, $C_{1-3}$-alkyloxy, difluoromethyl, trifluoromethyl, difluoromethoxy, trifluoromethoxy or cyano group, by the heteroaryl groups mentioned in the definition of the above groups is meant a pyridyl, pyridazinyl, pyrimidinyl or pyrazinyl group, while said heteroaryl groups are each mono- or disubstituted by the group $R^6$, while the substituents may be identical or different and unless otherwise stated, said alkyl groups may be straight-chained or branched, or a tautomer, stereoisomer, mixture or salt thereof.

2. A bicyclic heterocycle of formula I according to claim 1, wherein $R^a$ denotes a hydrogen atom, $R^b$ denotes a phenyl group substituted by the groups $R^1$ to $R^3$, where $R^1$ denotes a hydrogen, fluorine, chlorine or bromine atom, a methyl, trifluoromethyl or ethynyl group, a phenyloxy or phenylmethoxy group, wherein the phenyl moiety of said groups is optionally substituted by a fluorine or chlorine atom, or a pyridinyloxy or pyridinylmethoxy group, wherein the pyridinyl moiety of said groups is optionally substituted by a methyl or trifluoromethyl group, $R^2$ denotes a hydrogen, fluorine or chlorine atom and $R^3$ denotes a hydrogen atom, $R^c$ denotes a hydrogen atom, a $C_{1-3}$-alkyloxy group, a $C_{4-6}$-cycloalkyloxy or $C_{3-6}$-cycloalkyl-$C_{1-2}$-alkyloxy-group, a tetrahydrofuran-3-yloxy, tetrahydropyran-3-yloxy, tetrahydropyran-4-yloxy, tetrahydrofuranyl-$C_{1-2}$-alkyloxy or tetrahydropyranyl-$C_{1-2}$-alkyloxy group, an ethyloxy group which is substituted in the 2 position by a group $R^4$, where $R^4$ denotes a hydroxy, $C_{1-3}$-alkyloxy, amino, $C_{1-3}$-alkylamino, di-($C_{1-3}$-alkyl)amino, bis-(2-methoxyethyl)-amino, pyrrolidin-1-yl, piperidin-1-yl, homopiperidin-1-yl, morpholin-4-yl, homomorpholin-4-yl, piperazin-1-yl, 4-($C_{1-3}$-alkyl)-piperazin-1-yl, homopiperazin-1-yl, or 4-($C_{1-3}$-alkyl)-homopiperazin-1-yl group, a propyloxy group which is substituted in the 3 position by $R^4$, a butyloxy group which is substituted in the 4 position by $R^4$, A denotes an imino group, B denotes a carbonyl or sulphonyl group, C denotes a 1,1-vinylene, 1,2-vinylene or ethynylene group, D denotes a methylene, 1,1-ethylene or 1,2-ethylene group, E denotes a piperidin-1-yl group wherein two hydrogen atoms on the carbon skeleton are replaced by a straight-chain alkylene bridge, this bridge containing 2 to 5 carbon atoms if the two hydrogen atoms are located on the same carbon atom, or 1 to 4 carbon atoms if the two hydrogen atoms are located on adjacent carbon atoms, or 1 to 3 carbon atoms if the two hydrogen atoms are located on carbon atoms which are separated by one atom, or 1 or 2 carbon atoms if the two hydrogen atoms are located on carbon atoms which are separated by two atoms, while the said piperidin-1-yl groups may each additionally be substituted by one or two $C_{1-3}$-alkyl groups, a piperazin-1-yl group wherein two hydrogen atoms on the carbon skeleton are replaced by a straight-chain alkylene bridge, this bridge containing 2 to 5 carbon atoms if the two hydrogen atoms are located on the same carbon atom, or 1 to 4 carbon atoms if the two hydrogen atoms are located on adjacent carbon atoms, or 1 to 3 carbon atoms if the two hydrogen atoms are located on carbon atoms which are separated by one atom, or 1 or 2 carbon atoms if the two hydrogen atoms are located on carbon atoms which are separated by two atoms, while said piperazin-1-yl groups may each additionally be substituted by one or two $C_{1-3}$-alkyl groups, or a morpholin-4-yl group wherein two hydrogen atoms on the carbon skeleton are replaced by a straight-chain alkylene bridge, this bridge containing 2 to 5 carbon atoms if the two hydrogen atoms are located on the same carbon atom, or 1 to 4 carbon atoms if the two hydrogen atoms are located on adjacent carbon atoms, or 1 to 3 carbon atoms if the two hydrogen atoms are located on carbon atoms which are separated by one atom, or 1 or 2 carbon atoms if the two hydrogen atoms are located on carbon atoms which are separated by two atoms, while said morpholin-4-yl groups may each additionally be substituted by one or two $C_{1-3}$-alkyl groups, and X represents a nitrogen atom, while, unless otherwise stated, said alkyl groups may be straight-chain or branched, or a tautomer, stereoisomer, mixture or salt thereof.

3. A bicyclic heterocycle of formula 1 according to claim 1, wherein $R^a$ denotes a hydrogen atom, $R^b$ denotes a 3-ethynylphenyl, 3-bromophenyl, 3,4-difluorophenyl or 3-chloro-4-fluoro-phenyl group, $R^c$ denotes a hydrogen atom, a methoxy, ethyloxy, 2-(methoxy)ethyloxy, 3-(morpholin-4-yl)propyloxy, cyclobutyloxy, cyclopentyloxy, cyclohexyloxy, cyclopropylmethoxy, cyclopentylmethoxy, tetrahydrofuran-3-yloxy, tetrahydropyran-3-yloxy, tetrahydropyran-4-yloxy, tetrahydrofuran-2-ylmethoxy, tetrahydrofuran-3-ylmethoxy or tetrahydropyran-4-ylmethoxy group, A denotes an imino group, B denotes a carbonyl group, C denotes a 1,2-vinylene group, D denotes a methylene group, E denotes a 2-aza-bicyclo[2.2.1]hept-2-yl, 2,5-diaza-bicyclo[2.2.1]hept-2-yl, 5-methyl-2,5-diaza-bicyclo[2.2.1]hept-2-yl, 2-oxa-5-aza-bicyclo[2.2.1]hept-5-yl, 2-aza-bicyclo[2.2.2]oct-2-yl, 3-aza-bicyclo[3.2.1]oct-3-yl, 8-aza-bicyclo[3.2.1]oct-8-yl, 3,8-diaza-bicyclo[3.2.1]oct-3-yl, 8-methyl-3,8-diaza-bicyclo[3.2.1]oct-3-yl, 3,8-diaza-bicyclo[3.2.1]oct-8-yl, 3-methyl-3,8-diaza-bicyclo[3.2.1]oct-8-yl, 3-oxa-8-aza-bicyclo[3.2.1]oct-8-yl or 8-oxa-3-aza-bicyclo[3.2.1]oct-3-yl group and X denotes a nitrogen atom, or a tautomer, stereoisomer, mixture or salt thereof.

4. A bicyclic heterocycle of formula 1 according to claim 1, wherein $R^a$ denotes a hydrogen atom, $R^b$ denotes a 3-chloro-4-fluoro-phenyl group, $R^c$ denotes a tetrahydrofuran-3-yloxy, cyclopentyloxy or cyclopropylmethoxy group, A denotes an imino group, B denotes a carbonyl group, C denotes a 1,2-vinylene group, D denotes a methylene group, E denotes a 2-oxa-5-aza-bicyclo[2.2.1]hept-5-yl group, a 3-oxa-8-aza-bicyclo[3.2.1]oct-8-yl group or an 8-oxa-3-aza-bicyclo[3.2.1]oct-3-yl group and X denotes a nitrogen atom, or a tautomer, stereoisomer, mixture or salt thereof.

5. A compound according to claim 1 selected from:
(a) 4-[(3-chloro-4-fluoro-phenyl)amino]-6-{[4-((1S,4S)-2-oxa-5-aza-bicyclo[2.2.1]hept-5-yl)-1-oxo-2-buten-1-yl]amino}-7-cyclopropylmethoxy-quinazoline,
(b) 4-[(3-chloro-4-fluoro-phenyl)amino]-6-{[4-((1S,4S)-2-oxa-5-aza-bicyclo[2.2.1]hept-5-yl)-1-oxo-2-buten-1-yl]amino}-7-cyclopentyloxy-quinazoline,
(c) 4-[(3-chloro-4-fluoro-phenyl)amino]-6-{[4-((1S,4S)-2-oxa-5-aza-bicyclo[2.2.1]hept-5-yl)-1-oxo-2-buten-1-yl]amino}-7-[(S)-(tetrahydrofuran-3-yl)oxy]-quinazoline,
(d) 4-[(3-chloro-4-fluoro-phenyl)amino]-6-{[4-(3-oxa-8-aza-bicyclo[3.2.1]oct-8-yl)-1-oxo-2-buten-1-yl]amino}-7-[(S)-(tetrahydrofuran-3-yl)oxy]-quinazoline,
(e) 4-[(3-chloro-4-fluoro-phenyl)amino]-6-{[4-((1R,4R)-2-oxa-5-aza-bicyclo[2.2.1]hept-5-yl)-1-oxo-2-buten-1-yl]amino}-7-[(S)-(tetrahydrofuran-3-yl)oxy]-quinazoline,
(f) 4-[(3-chloro-4-fluoro-phenyl)amino]-6-{[4-(8-oxa-3-aza-bicyclo[3.2.1]oct-3-yl)-1-oxo-2-buten-1-yl]amino}-7-[(S)-(tetrahydrofuran-3-yl)oxy]-quinazoline,
(g) 4-[(3-chloro-4-fluoro-phenyl)amino]-6-{[4-((1R,4R)-2-oxa-5-aza-bicyclo[2.2.1]hept-5-yl)-1-oxo-2-buten-1-yl]amino}-7-[(R)-(tetrahydrofuran-3-yl)oxy]-quinazoline and
(h) 4-[(3-chloro-4-fluoro-phenyl)amino]-6-{[4-((1S,4S)-2-oxa-5-aza-bicyclo[2.2.1]hept-5-yl)-1-oxo-2-buten-1-yl]amino}-7-[(R)-(tetrahydrofuran-3-yl)oxy]-quinazoline, or a salt thereof.

6. Pharmaceutical compositions containing a compound according to claim 1 together with one or more inert carriers and/or diluents.

7. A physiologically acceptable salt according to claim 6 with organic or inorganic acids and bases.

8. A physiologically acceptable salt of the compound according claim 1 with inorganic or organic acids or bases.

* * * * *